United States Patent
Iverson et al.

(10) Patent No.: US 10,851,942 B1
(45) Date of Patent: Dec. 1, 2020

(54) VIBRATORY SYSTEM LUBRICATION REMAINING USEFUL LIFE

(71) Applicant: Caterpillar Paving Products Inc., Brooklyn Park, MN (US)

(72) Inventors: Robert K. Iverson, Maple Grove, MN (US); Craig R. Fausch, Nowthen, MN (US)

(73) Assignee: Caterpillar Paving Products Inc., Brooklyn Park, MN (US)

( * ) Notice: Subject to any disclaimer, the term of this patent is extended or adjusted under 35 U.S.C. 154(b) by 0 days.

(21) Appl. No.: 16/426,547

(22) Filed: May 30, 2019

(51) Int. Cl.
*E01C 19/00* (2006.01)
*F16N 29/00* (2006.01)
*E01C 19/28* (2006.01)
*G01N 33/28* (2006.01)
*G01N 29/50* (2006.01)
*G07C 3/00* (2006.01)
*G01N 29/12* (2006.01)

(52) U.S. Cl.
CPC ............ *F16N 29/00* (2013.01); *E01C 19/282* (2013.01); *E01C 19/286* (2013.01); *G01N 29/12* (2013.01); *G01N 29/50* (2013.01); *G01N 33/2888* (2013.01); *G07C 3/005* (2013.01); *E01C 2301/30* (2013.01); *F16N 2210/14* (2013.01)

(58) Field of Classification Search
CPC .... F16N 29/00; F16N 2210/14; E01C 19/282; E01C 19/286; E01C 2301/30; G01N 29/12; G01N 29/50; G01N 33/2888; G07C 3/005
USPC ......... 404/72, 84.05–95, 101–108, 112, 117, 404/118
See application file for complete search history.

(56) References Cited

U.S. PATENT DOCUMENTS

| | | | | |
|---|---|---|---|---|
| 4,759,659 A | * | 7/1988 | Copie | B06B 1/165 366/125 |
| 6,007,273 A | * | 12/1999 | Magee | E01C 19/238 404/122 |
| 6,324,899 B1 | * | 12/2001 | Discenzo | F16C 19/52 340/631 |
| 6,637,280 B2 | | 10/2003 | Potts | |
| 2003/0167141 A1 | * | 9/2003 | Staszewski | G01N 29/075 702/77 |
| 2013/0243526 A1 | * | 9/2013 | Williamson | F16F 15/08 404/133.1 |
| 2017/0306575 A1 | * | 10/2017 | Utterodt | E01C 19/282 |
| 2018/0011065 A1 | * | 1/2018 | Bowers, III | G01N 29/4427 |
| 2018/0172636 A1 | | 6/2018 | Shaffer | |
| 2019/0048536 A1 | * | 2/2019 | Muir | E01C 23/088 |

(Continued)

FOREIGN PATENT DOCUMENTS

| | | |
|---|---|---|
| JP | H07174685 | 7/1995 |
| JP | 2000017659 | 1/2000 |

*Primary Examiner* — Raymond W Addie
(74) *Attorney, Agent, or Firm* — Schwegman, Lundberg & Woessner; Jeff A. Greene

(57) ABSTRACT

A work machine includes a compactor drum, a controller, and an output device. The compactor drum includes a vibratory system, which includes at least one bearing that supports rotation of the vibratory system within the compactor drum, and lubricant received by the at least one bearing. The controller is configured to monitor at least one physical property of the vibratory system over a specified time and project a remaining useful life of the lubricant based on the at least one physical property. The output device is configured to generate an output indicative of the remaining useful life.

20 Claims, 3 Drawing Sheets

(56) References Cited

U.S. PATENT DOCUMENTS

2019/0120425 A1* 4/2019 Gossard .................. F16N 29/02
2019/0257409 A1* 8/2019 Bourgault ............... F16H 55/30
2019/0382966 A1* 12/2019 Laugwitz ................. G01N 3/34

* cited by examiner

VIBRATORY SYSTEM LUBRICATION REMAINING USEFUL LIFE

TECHNICAL FIELD

The present application relates generally to work machines. More particularly, the present application relates to lubrication for vibratory systems.

BACKGROUND

Vibratory systems, such as vibratory compactors, can be used for compacting soil substrates. More particularly, after application of an asphalt layer on a ground surface, a vibratory compactor can be moved over the ground surface in order to achieve a planar ground surface. The compactor can include single or dual vibrating compactor drums. The compactor drums generally include a vibration system that transfers vibrations to the ground surface in order to impose compaction forces for leveling the ground surface.

U.S. Pat. No. 6,637,280 describes an example vibratory mechanism that includes motors connected to drive eccentric weights. Vibratory systems like this one can include several bearings. Lubricant, such as oil, is generally used to protect the bearings and prevent failure of the bearings. Conventionally, oil is changed for the vibratory compactor every year or 1,000 hours.

SUMMARY OF THE INVENTION

In one example, work machine includes a compactor drum, a controller, and an output device. The compactor drum includes a vibratory system, which includes at least one bearing that supports rotation of the vibratory system within the compactor drum, and lubricant received by the at least one bearing. The controller is configured to monitor at least one physical property of the vibratory system over a specified time and project a remaining useful life of the lubricant based on the at least one physical property. The output device is configured to generate an output indicative of the remaining useful life.

In another example, A method of estimating a remaining useful life of a lubricant for a vibratory system of a compaction machine includes receiving, by at least one bearing of the vibratory system, a lubricant; monitoring, by a controller, at least one physical property of the vibratory system over a specified time; projecting, by the controller, a remaining useful life of the lubricant based on the at least one property of the vibratory system over the specified time; and outputting an indication of the remaining useful life of the lubricant for an operator of the vibratory system.

In another example, a vibratory compactor that includes a compactor drum, also includes a vibratory system, a controller, and an output device. The vibratory system is positioned within the compactor drum and includes at least one bearing that supports rotation of the vibratory system within the compactor drum, and lubricant received by the at least one bearing. The controller is configured to monitor a plurality of physical properties of the vibratory system and project a remaining useful life of the lubricant based on the plurality of physical properties. The output device is configured to generate an output indicative of the remaining useful life.

DETAILED DESCRIPTION

Figure 1:
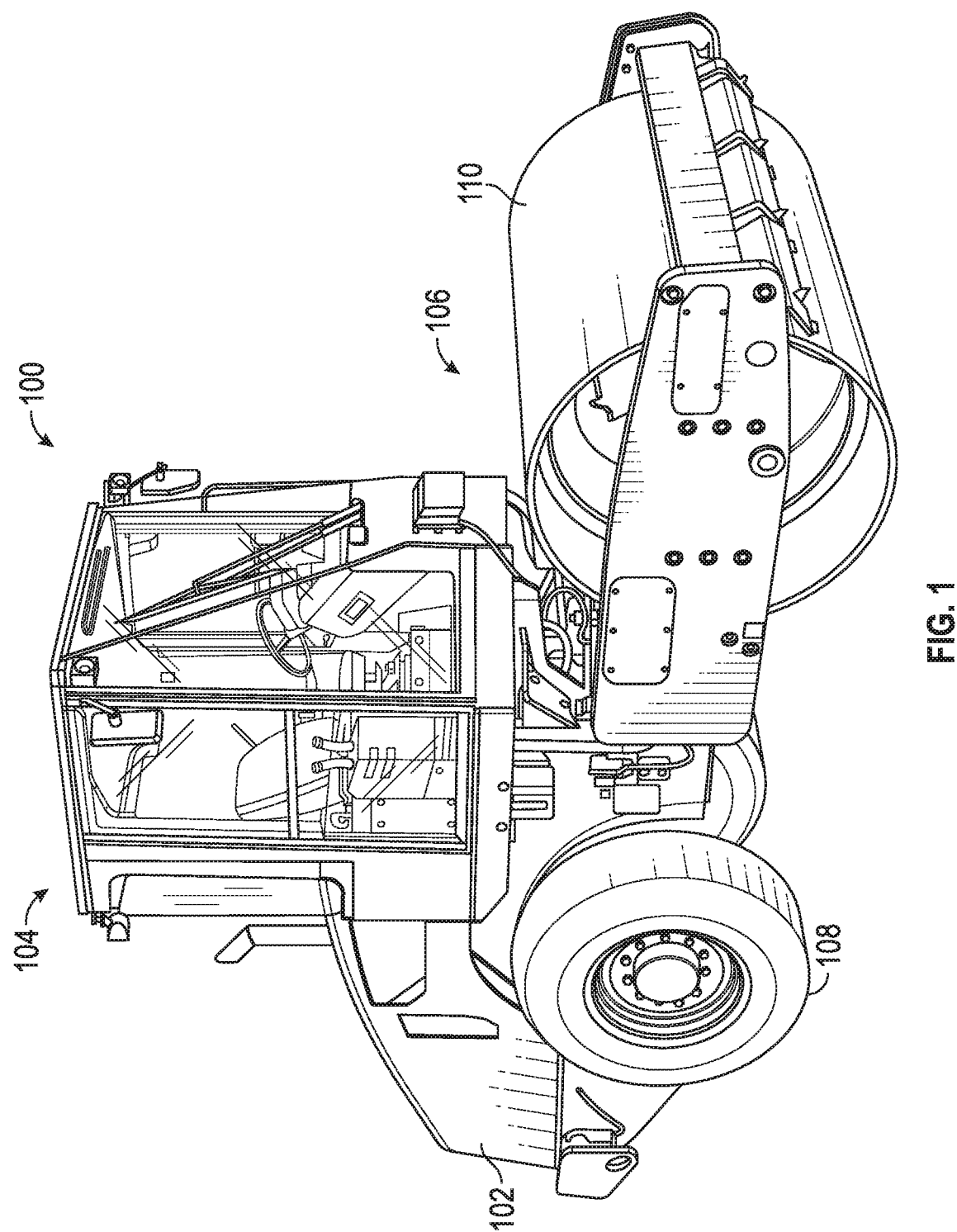
FIG. 1 is a perspective view illustrating an example vibratory compaction machine.

FIG. 1 is a perspective view illustrating an example vibratory compaction machine 100. While illustrated as a compaction machine, the systems and methods disclosed herein can be applied to any work machine that includes a vibratory system. The vibratory compaction machine 100 is adapted to move over a ground surface made of asphalt, gravel, or any other surface, in order to compact it. The vibratory compaction machine 100 may be a manual, autonomous, or semi-autonomous machine, for example.

The vibratory compaction machine 100 includes a frame 102, an operator cab 104, a compactor drum 106, and wheels 108. The compactor drum 106 includes an outer surface 110 that contacts the ground. An engine can be mounted on the vibratory compaction machine 100 for providing propulsion power to the vibratory compaction machine 100, The engine may be an internal combustion engine such as a compression ignition diesel engine, or any other engine, including a gas turbine engine, for example. The operator cab 104 is mounted on the frame 102. For manual or semi-autonomous machines, an operator of the vibratory compaction machine 100 can be seated within the operator cab 104 to perform one or more machine operations.

The frame 102 is configured to rotatably support the compactor drum 106, which moves along, and provides compaction for, the ground surface. The compactor drum 106 acts as a ground engaging member that rotates about a respective axis thereby propelling the vibratory compaction machine 100 on the ground surface along with the wheels 108. In other examples, the wheels 108 can be replaced with a second compactor drum that operates in a similar manner to the compactor drum 106. The outer surface 110 of a drum shell of the compactor drum 106 contacts the ground surface as the vibratory compaction machine 100 moves along the ground surface.

A drive motor and a transmission gear can be mounted within the compactor drum 106. In one example, the drive motor may be an electric motor, for example. The drive motor and the transmission gear enable the compactor drum 106 to be rotated and thus the vibratory compaction machine 100 to move over the ground surface.

Figure 2:
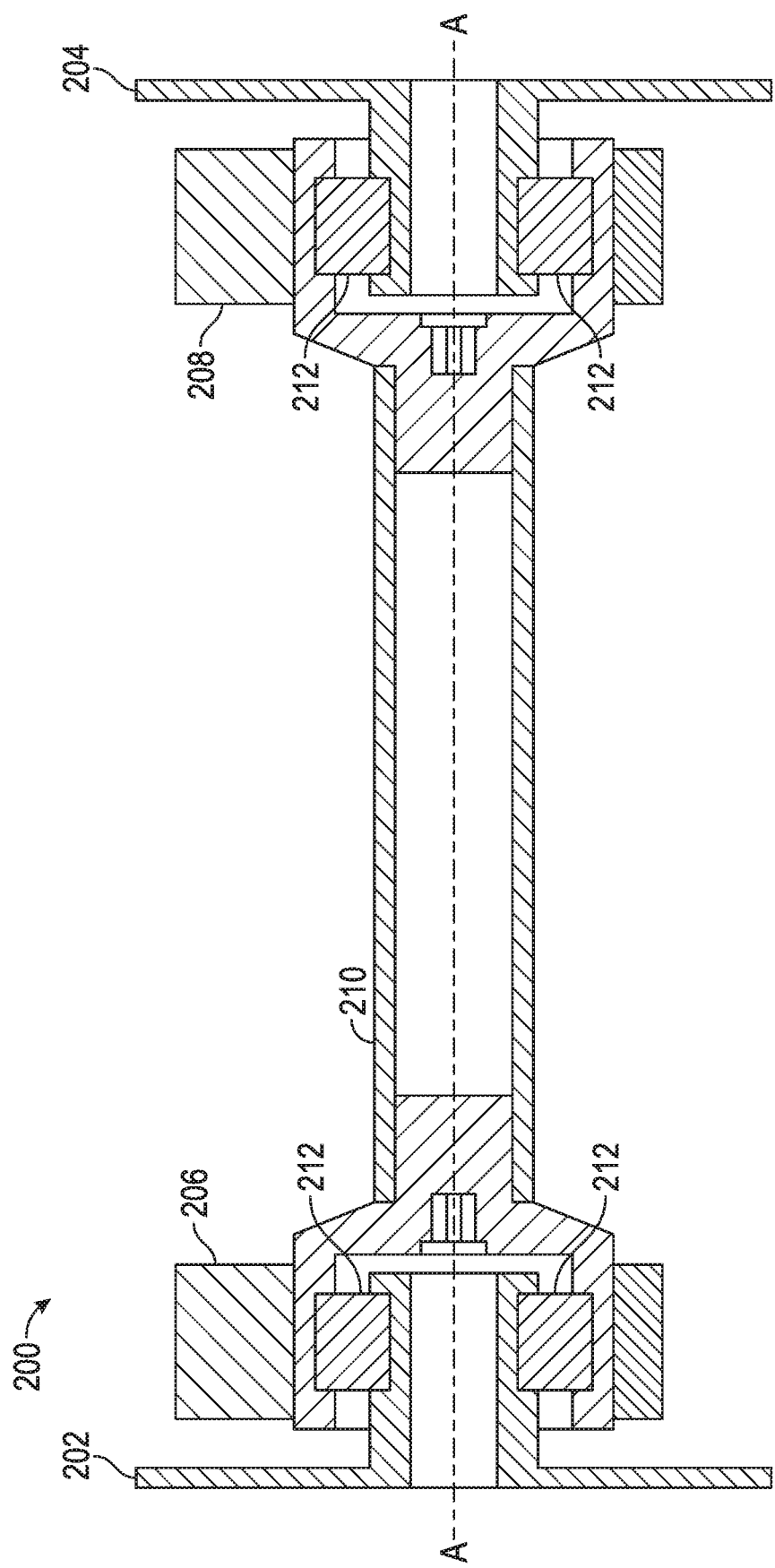
FIG. 2 is a cross-sectional view illustrating an example vibratory system within a compactor drum.

FIG. 2 is a cross-sectional view illustrating an example vibratory system 200 positioned within the compactor drum 106. The vibratory system 200 can also be used in a second compactor drum of a compaction machine, for example. The vibratory system 200 is configured to generate vibrations in the compactor drum 106 and includes support structures 202 and 204, vibratory mechanisms 206 and 208, shaft 210, and bearings 212. In an example, the vibratory system 200 can be a dual amplitude vibratory system. In other examples, the vibratory system 200 can be any vibratory system configured to provide vibration for the compactor drum 106 and can include components in addition to, or in place of, components illustrated in FIG. 2. The support structures 202 and 204 can be circular plates that are fixedly mounted within the compactor drum 106, for example, or any other structure configured to attach the vibratory system 200 to the compactor drum 106. For example, the support structures 202 and 204 may be welded to an inner surface of the compactor drum 106.

The vibratory system 200 includes two vibratory mechanisms 206 and 208. In other examples, the vibratory system 200 can include any number of vibratory mechanisms. The vibratory mechanisms 204 and 206 can be eccentric weights, for example, that rotate together as a unitary component during an operation of the vibratory system 200. The shaft 210 connects the vibratory mechanism 204 with the vibratory mechanism 206. The vibratory mechanisms 206 and 208 can generate the vibrations in the compactor drum 106 based on activation of a vibratory pump, motor, or both, which may be mounted on the first support structure 202, or at any other desirable location within the compactor drum 106. The vibratory pump and/or motor may be hydraulic and/or electric, for example.

The vibratory mechanisms 206 and 208 can rotate separately from the compactor drum 106. The bearings 212 enable independent rotation of the compactor drum 106 about the vibratory system 200. The vibratory pump and/or motor may include a drive shaft, for example, coupled to drive the shaft 210. Thus, when the vibratory and/or motor is enabled, the shaft 210 is driven, rotating the vibratory mechanisms 206 and 208 about the axis A to generate vibration within the compactor drum 106.

With the vibrations generated by the vibratory system 200, the compactor drum 106 moves up and down to compact the ground. The amount of distance from the ground that the compactor drum 106 moves due to the vibrations is the vibration amplitude. In some examples, the vibratory system 200 may be configured as a dual-amplitude system in which the vibratory system 200 can rotate in one direction to generate vibrations with a first amplitude, and in another direction to generate vibrations with a second amplitude, for example. In other examples, the vibratory system may permit vibration at any number of amplitudes. The pump and/or motor may also be configured to generate vibrations at multiple vibratory frequencies.

The bearings 212 receive a lubricant, such as oil, grease, or any other lubricant, to reduce friction. Over time, the lubricant wears out and must be replaced. Conventionally, lubricant is replaced every year or 1,000 hours of operation. However, the lubricant can wear faster or slower based on the operation of the vibratory system 200. Several physical properties of the vibratory system 200 can contribute to the wear of the lubricant including, but not limited to, the amplitude of vibration, the frequency of vibration, and temperature of the vibratory system 200.

Figure 3:
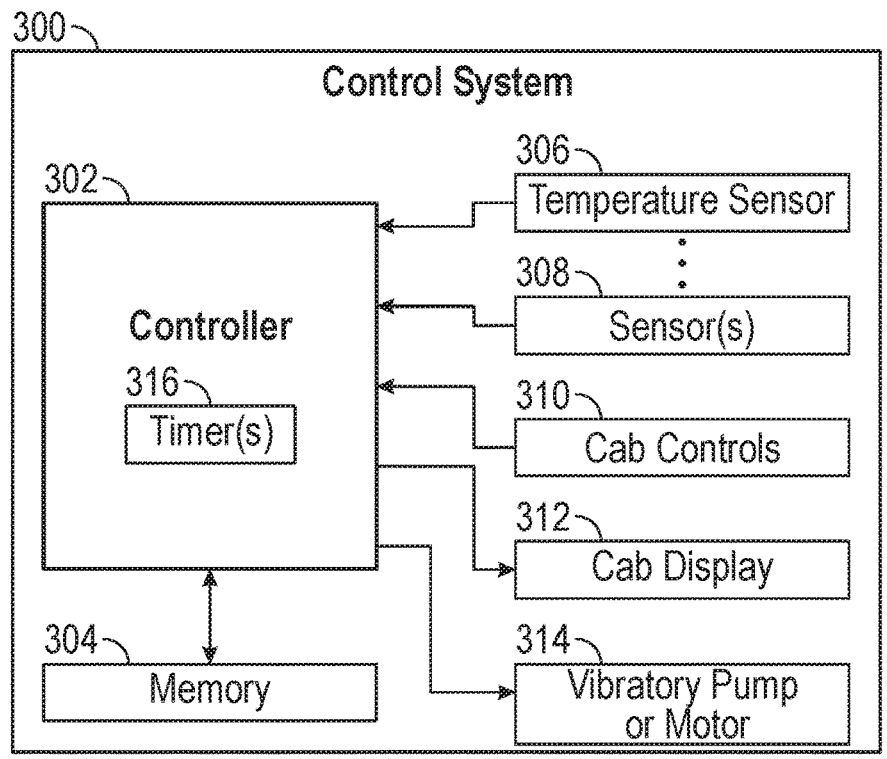
FIG. 3 is a block diagram illustrating an example control system for a vibratory compactor machine.

FIG. 3 is a block diagram illustrating a control system 300 for a compaction machine, such as the vibratory compaction machine 100. The control system 300 includes a controller 302, a memory 304, a temperature sensor 306, other sensors 308, cab controls 310, cab display 312, and the vibratory pump and/or motor 314. The controller 302 can include one or more timer circuits 316. The cab controls 310 can be operated by an operator positioned within the cab 104. The operator can control the speed and operation of the compaction machine 100, as well as operation of the vibratory system 200 through control of the vibratory pump and/or motor 314. A display 312 or other output device can also be positioned within the cab 104 to provide output to an operator. In an example, the cab controls 310 and the display 312 may be a single device, such as a touchscreen, for example.

The controller 302 and memory 304 can include, for example, software, hardware, and combinations of hardware and software configured to execute several functions related to control of the compaction machine 100. In one example, the controller 302 and memory 304 can be an engine control module (ECM). The controller 302 can include an analog, digital, or combination analog and digital controller including a number of components. As examples, the controller 302 can include integrated circuit boards or ICB(s), printed circuit boards PCB(s), processor(s), data storage devices, switches, relays, or any other components. Examples of processors can include any, one or more of a microprocessor, a controller, a digital signal processor (DSP), an application specific integrated circuit (ASIC), a field-programmable gate array (FPGA), or equivalent discrete or integrated logic circuitry.

The memory 304 may include storage media to store and/or retrieve data or other information such as, for example, signals from the temperature sensor 306 and other sensors 308. Storage devices, in some examples, are described as a computer-readable storage medium. The memory 304 can be used to store program instructions for execution by processor(s) of the controller 302, for example. The memory 304, for example, are used by software, applications, algorithms, as examples, running on and/or executed by the controller 302. The memory 304 can include short-term and/or long-term memory and can be volatile and/or non-volatile. Examples of non-volatile storage elements include magnetic hard discs, optical discs, floppy discs, flash memories, or forms of electrically programmable memories (EPROM) or electrically erasable and programmable (EEPROM) memories. Examples of volatile memories include random access memories (RAM), dynamic random access memories (DRAM), static random access memories (SRAM), and other forms of volatile memories known in the art.

The temperature sensor 306 can be positioned within the compactor drum 106 near the vibratory system 200 or in any other location. Other sensors 308 can include accelerometers, phases sensors, speed sensors, or any other sensors configured to sense one or more of the physical properties of the compaction machine 100. For example, an accelerometer may be used to measure the actual vibrational characteristics or output of (e.g., the amplitude and the frequency of the vibrations produced by) the compactor drum 106. In operation, phase measurements provided by a phase sensor may be used by the controller 302 as a feedback signal to monitor and control the amplitude of the vibrations produced by the compactor drum 106. Similarly, the measurements provided by the speed sensor may be used by the controller 306 as a feedback signal to monitor and/or control the frequency of the vibrations produced by the compactor 100.

The controller 302 is configured to determine a remaining useful life of the lubricant of the vibratory system 200 based on observed physical properties of the vibratory system 200. The controller 302 may monitor the frequency of vibration, amplitude of vibration, and/or temperature of the compactor drum 106 over time. To monitor these physical properties, the controller 302 may monitor sensor data from the temperature sensor 306, the other sensors 308, and/or determine one or more of the properties based on current operating conditions. For example, the controller 302 may determine the vibratory frequency or amplitude of the vibratory system 200 based on current control inputs from the cab controls 310.

The controller 302 may use timers 316 or other circuitry to observe an amount of time at which the vibratory system is at an observed frequency, amplitude, and/or temperature. This data can be stored in the memory 304 over time and used as data points to project a remaining useful life of the lubricant. The remaining useful life may be determined using any approach based on the stored data points. For example, testing of the vibratory system 200 may be performed to determine a curve-fit for the physical properties over time with respect to lubricant remaining useful life. During actual operation of the compaction machine 100, this curve-fit can be applied to interpolate the remaining useful life using the stored data points data points.

The display 312 or other output device may be used to output an indication of the projected remaining useful life to an operator. In an example, the display 312 may be a single indicator light that illuminates when the lubrication needs to be changed. In another example, the display 312 may be a liquid crystal display (LCD) or other flat panel display configured to output image data. The display 312 can output the remaining useful life of the lubricant, the current life of the lubricant, the current vibratory frequency, the current amplitude, the current temperature, and/or any other desirable data.

By providing a remaining useful life of the lubricant, the lubricant can be changed only when necessary, and not based on a conservative time interval. This can extend the lubricant change interval, decreasing cost, and also limit exposure to debris due to decreased changing of the lubricant.

INDUSTRIAL APPLICABILITY

Figure 4:
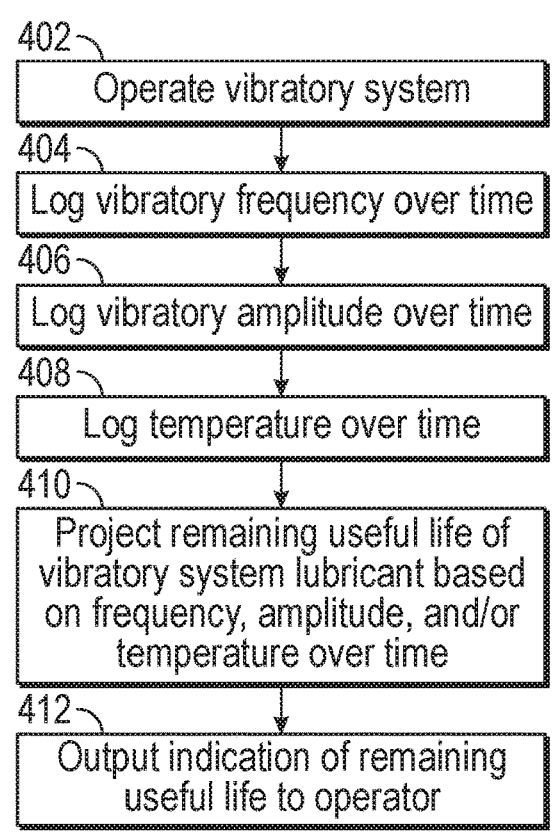
FIG. 4 is a flowchart illustrating a method of predicting a remaining useful life of lubricant for a vibratory system of a compaction machine.

In one illustrative example, a vibratory soil compactor is controlled by an operator. FIG. 4 is a flowchart illustrating a method 400 of projecting a remaining useful life of lubricant used by the vibratory soil compactor. Prior to beginning method 400, the lubrication is replaced for bearings of the vibratory system of the soil compactor. As seen in FIG. 4, at step 402, the operator controls the soil compactor to compact a ground surface. At step 404, during operation of the soil compactor, a controller can measure or otherwise determine the vibratory frequency of the vibratory system. The controller can log this information over any specified time period. The specified time period, for example, can be a duration of operation of the vibratory system of the soil compactor. In another example, the specified time period can be any operation of the soil compactor. Similarly, at step 406, during operation of the vibratory system, the controller can measure or otherwise determine the vibratory amplitude of the vibratory system, and at step 408, the controller can measure or otherwise determine a temperature of the vibratory system.

At step 410, the controller projects the remaining useful life of lubricant for the vibratory system using one or more of the monitored frequencies, amplitudes, and temperatures. The projection can be accomplished using any desired method. For example, interpolation can be used to project the remaining useful life of the lubricant based on collected data points regarding the monitored frequency, amplitude, and temperature over the specified time.

At step 412, an indication of the remaining useful life is output for an operator. For example, a display may be present within the cab of the vibratory soil compactor. The remaining useful life may be output on the display for the operator so that the operator can make an informed decision regarding replacing the lubricant. Conventionally, the lubricant is replaced every year or 1,000 hours. Using method 400, the lubricant can be changed only when necessary, and not based on a conservative time interval. This can extend the lubricant change interval, decreasing cost, and also limit exposure to debris due to decreased changing of the lubricant.

The above detailed description is intended to be illustrative, and not restrictive. The scope of the disclosure should, therefore, be determined with references to the appended claims, along with the full scope of equivalents to which such claims are entitled.

What is claimed is:

1. A work machine comprising:
    a compactor drum that comprises a vibratory system, the vibratory system comprising:
        at least one bearing that supports rotation of the vibratory system within the compactor drum; and
        lubricant received by the at least one bearing;
    a controller configured to monitor a plurality of physical properties of the vibratory system over a specified time and project a remaining useful life of the lubricant based on the plurality of physical properties; and
    an output device configured to generate an output indicative of the remaining useful life.

2. The work machine of claim 1, further comprising:
    an operator cab mounted to a frame of the work machine; and
    controls positioned within the operator cab configured to receive input from an operator and provide output to the controller to control the work machine; and
    wherein the output device is a display positioned within the operator cab.

3. The work machine of claim 1, wherein the vibratory system further comprises a pump or motor, and at least one vibratory mechanism positioned to induce vibrations within the compactor drum.

4. The work machine of claim 3, wherein the plurality of physical properties is one of an amplitude of the vibrations within the compactor drum or a frequency of the vibrations within the compactor drum.

5. The work machine of claim 3, further comprising a temperature sensor configured to provide a sensed temperature to the controller, wherein the controller is configured to determine a temperature related to the at least one bearing using the sensed temperature.

6. The work machine of claim 5, wherein the plurality of physical properties is one or more of an amplitude of the vibrations within the compactor drum, a frequency of the vibrations within the compactor drum, or the temperature related to the at least one bearing.

7. The work machine of claim 6, wherein the controller is configured to project the remaining useful life of the lubricant based on all of the amplitude of the vibrations, the frequency of the vibrations, and the temperature related to the at least one bearing.

8. A method of estimating a remaining useful life of a lubricant for a vibratory system of a compaction machine, the method comprising:
    receiving, by at least one bearing of the vibratory system, a lubricant;
    monitoring, by a controller, a plurality of physical properties of the vibratory system over a specified time;
    projecting, by the controller, a remaining useful life of the lubricant based on the a plurality of physical properties of the vibratory system over the specified time; and
    outputting an indication of the remaining useful life of the lubricant for an operator of the vibratory system.

9. The method of claim 8, further comprising inducing, by a vibratory mechanism of the vibratory system, vibrations within the compactor drum.

10. The method of claim 9, wherein monitoring, by the controller, the plurality of physical properties of the vibratory system over the specified time comprises monitoring at least one of an amplitude of the vibrations within the compactor drum or a frequency of the vibrations within the compactor drum.

11. The method of claim 9, further comprising monitoring a temperature related to the at least one bearing using the sensed temperature.

12. The method of claim 11, wherein monitoring, by the controller, the plurality of physical properties of the vibratory system over the specified time comprises monitoring one or more of an amplitude of the vibrations within the compactor drum, a frequency of the vibrations within the compactor drum, or the temperature related to the at least one bearing.

13. The method of claim 12, wherein projecting, by the controller, the remaining useful life of the lubricant based on the plurality of physical properties of the vibratory system over the specified time comprises projecting the remaining useful life of the lubricant based on all of the amplitude of the vibrations, the frequency of the vibrations, and the temperature related to the at least one bearing.

14. A vibratory compactor that includes a compactor drum, the vibratory compactor comprising:
   a vibratory system positioned within the compactor drum, the vibratory system comprising:
      at least one bearing that supports rotation of the vibratory system within the compactor drum; and
      lubricant received by the at least one bearing;
   a controller configured to monitor a plurality of physical properties of the vibratory system and project a remaining useful life of the lubricant based on the plurality of physical properties; and
   an output device configured to generate an output indicative of the remaining useful life.

15. The vibratory compactor of claim 14, further comprising:
   an operator cab mounted to a frame of the vibratory compactor; and
   controls positioned within the operator cab configured to receive input from an operator and provide output to the controller to control the vibratory compactor; and
   wherein the output device is a display positioned within the operator cab.

16. The vibratory compactor of claim 14, wherein the vibratory system further comprises a pump or motor, and at least one vibratory mechanism positioned to induce vibrations within the compactor drum.

17. The vibratory compactor of claim 16, wherein the plurality of physical properties comprise at least one of an amplitude of the vibrations within the compactor drum or a frequency of the vibrations within the compactor drum.

18. The vibratory compactor of claim 16, further comprising a temperature sensor configured to provide a sensed temperature to the controller, wherein the controller is configured to determine a temperature related to the at least one bearing using the sensed temperature.

19. The vibratory compactor of claim 18, wherein the plurality of physical properties comprise at least one of an amplitude of the vibrations within the compactor drum, a frequency of the vibrations within the compactor drum, or the temperature related to the at least one bearing.

20. The vibratory compactor of claim 19, wherein the controller is configured to project the remaining useful life of the lubricant based on all of the amplitude of the vibrations, the frequency of the vibrations, and the temperature related to the at least one bearing.

* * * * *